US009181156B2

(12) United States Patent
Ko et al.

(10) Patent No.: US 9,181,156 B2
(45) Date of Patent: *Nov. 10, 2015

(54) APPARATUS FOR PRODUCING ALCOHOLS FROM OLEFINS

(71) Applicant: LG Chem, Ltd., Seoul (KR)

(72) Inventors: Dong-Hyun Ko, Daejeon (KR); Sung-Shik Eom, Daejeon (KR); Yong-Jin Choe, Daejeon (KR); Chan-Hong Lee, Daejeon (KR); Moo-Ho Hong, Daejeon (KR); O-Hak Kwon, Daejeon (KR); Dae-Chul Kim, Daejeon (KR); Jae-Hui Choi, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/061,045

(22) Filed: Oct. 23, 2013

(65) Prior Publication Data

US 2014/0051893 A1 Feb. 20, 2014

Related U.S. Application Data

(63) Continuation of application No. 13/121,755, filed on Mar. 30, 2011, now Pat. No. 8,673,244, which is a continuation of application No. PCT/KR2010/000283, filed on Jan. 15, 2010.

(30) Foreign Application Priority Data

Jan. 16, 2009 (KR) .................. 10-2009-0003732

(51) Int. Cl.
| | |
|---|---|
| C07C 29/141 | (2006.01) |
| C07C 45/50 | (2006.01) |
| B01J 23/72 | (2006.01) |
| B01J 25/02 | (2006.01) |
| B01J 31/20 | (2006.01) |
| B01J 31/22 | (2006.01) |
| B01J 31/24 | (2006.01) |

(52) U.S. Cl.
CPC ............... *C07C 29/141* (2013.01); *C07C 45/50* (2013.01); *B01J 23/72* (2013.01); *B01J 25/02* (2013.01);
(Continued)

(58) Field of Classification Search
USPC .......... 422/234, 235, 608, 610; 568/882, 883, 568/451
See application file for complete search history.

(56) References Cited

U.S. PATENT DOCUMENTS

| 2,638,487 A | 5/1953 | Hengstebeck et al. |
| 3,847,989 A * | 11/1974 | Platz et al. ................ 564/385 |

(Continued)

FOREIGN PATENT DOCUMENTS

| CN | 1255476 A | 6/2000 |
| CN | 1312785 A | 9/2001 |

(Continued)

OTHER PUBLICATIONS

Supplementary European Search Report for Application No. EP10731408 dated May 25, 2012.

*Primary Examiner* — Lessanework Seifu
(74) *Attorney, Agent, or Firm* — Lerner, David, Littemberg, Krumholz & Mentlik, LLP

(57) ABSTRACT

The present invention relates to an apparatus for producing alcohols from olefins, comprising: a hydroformylation reactor wherein aldehydes are produced from olefins; a catalyst/aldehydes separator; a hydrogenation reactor wherein the aldehydes are hydrogenated to produce alcohols; and a distillation column. The hydroformylation reactor is equipped with a distributor plate, which has a broad contact surface for providing sufficient reaction area for reactants such as olefins and synthesis gas, and allows the reaction mixture to circulate and mix sufficiently, which contribute to excellent efficiency in terms of production of aldehydes. In addition, the hydrogenation reactor suppresses sub-reactions to improve the production yield of alcohols.

14 Claims, 8 Drawing Sheets

(52) U.S. Cl.
CPC ............... *B01J 31/20* (2013.01); *B01J 31/2234* (2013.01); *B01J 31/2404* (2013.01); *B01J 2231/321* (2013.01); *B01J 2531/822* (2013.01)

(56) References Cited

U.S. PATENT DOCUMENTS

| | | |
|---|---|---|
| 4,312,837 A | 1/1982 | Papp et al. |
| 5,154,898 A | 10/1992 | Ajinkya et al. |
| 5,763,678 A | 6/1998 | Beckers et al. |
| 6,407,295 B1 | 6/2002 | Kaizik et al. |
| 6,642,420 B1 | 11/2003 | Zehner et al. |
| 2001/0003785 A1 | 6/2001 | Protzmann et al. |
| 2006/0004231 A1 | 1/2006 | Zehner et al. |
| 2007/0282132 A1 | 12/2007 | Beadle et al. |

FOREIGN PATENT DOCUMENTS

| | | |
|---|---|---|
| CN | 1894183 A | 1/2007 |
| DE | 19836807 A1 | 2/2000 |
| KR | 20080104710 A | 12/2008 |
| KR | 20080105004 A | 12/2008 |
| WO | 2005058782 A1 | 6/2005 |
| WO | 2008147129 A1 | 12/2008 |

* cited by examiner

FIG. 1
(a)
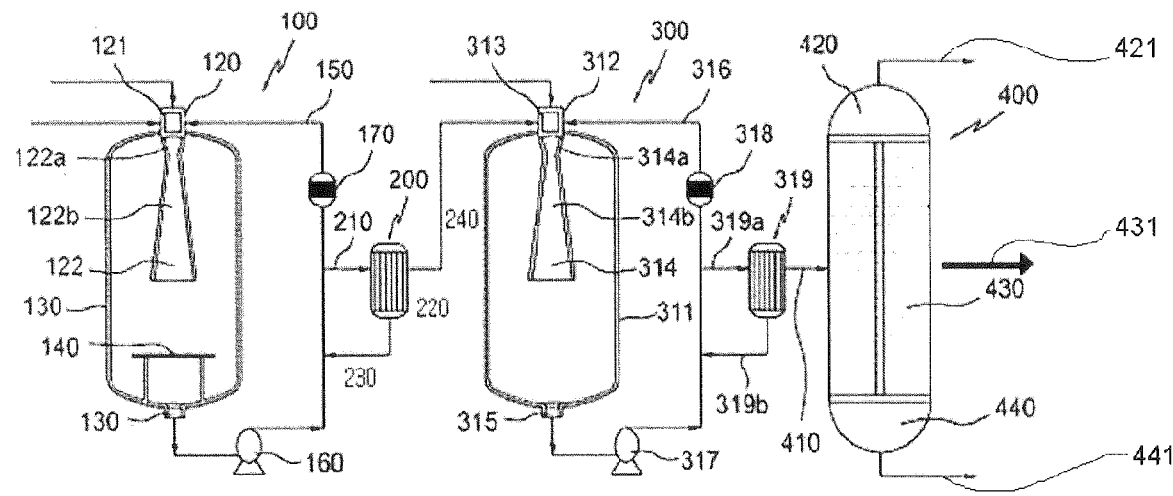
(b)
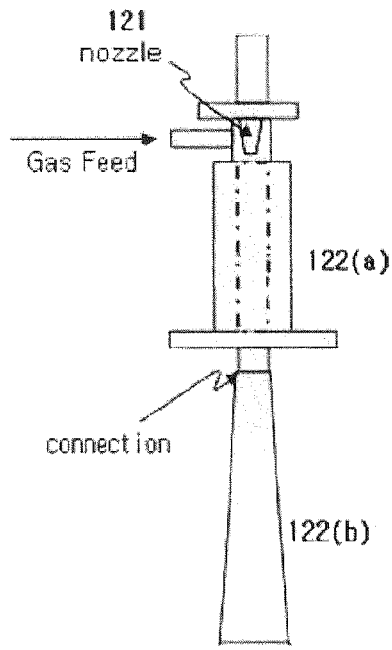

APPARATUS FOR PRODUCING ALCOHOLS FROM OLEFINS

CROSS-REFERENCE TO RELATED APPLICATIONS

The present application is a continuation of U.S. patent application Ser. No. 13/121,755, filed Mar. 30, 2011, which is a continuation application of International Application No. PCT/KR2010/000283, filed Jan. 15, 2010, which claims the benefit of Korean Patent Application No. 10-2009-0003732, filed on Jan. 16, 2009. The disclosures of said applications are incorporated by reference herein.

TECHNICAL FIELD

The present invention relates to an apparatus for producing alcohols from olefins, and more specifically, to an apparatus for producing alcohols from olefins, in which the apparatus comprises a hydroformylation reactor; a catalyst/aldehydes separator; a hydrogenation reactor; and a distillation column.

BACKGROUND ART

A hyroformylation reaction that is generally well known as OXO reaction is a process for producing linear (normal) and branched (iso) aldehyde, in which the olefin is added with one carbon number by reacting all kinds of olefins and synthesis gas ($CO/H_2$) under presence of metal catalyst and ligand.

All kinds of aldehydes that are synthesized by OXO reaction are modified into alcohol and acid that are aldehyde derivatives through an oxidation or reduction reaction. Also, they can be modified into various acids and alcohols comprising long alkyl group through an oxidation or reduction reaction after a condensation reaction, such as aldol, and the like. Those alcohols and acids are being used as a raw material for solvent, additive and all kinds of plasticizers.

The representative example of the hydroformylation is to produce octanol (2-ethylhexanol) from propylene using a rhodium-based catalyst. Octanol is mainly used as a raw material for PVC plasticizer, such as dioctyl phthalate (DOP), and also as an intermediate raw material for synthesis lubricant, surfactant, and the like.

Propylene is injected with a catalyst into OXO reactor using a catalyst to produce normal-butylaldehydes and iso-butylaldehydes. The produced aldehydes mixture is transferred to a separator along with catalyst mixture to separate into hydrocarbon and catalyst mixture, and then the catalyst mixture is circulated into the reactor and the hydrocarbon is transferred to a stripper. The hydrocarbon in the stripper is stripped by fresh synthesis gas to recover non-reacted propylene and synthesis gas into OXO reactor and transfer butylaldehydes to a fractionation column thereby separating normal- and iso-butylaldehydes, respectively. Normal-butylaldehydes of the fractionation column bottom is transferred to a hydrotreated reactor, and then adding hydrogen produces n-butanol. Alternatively, normal-butylaldehydes is introduced into an aldol condensation reactor to produce 2-ethylhexanal through a condensation and dehydration reaction, and then is transferred to the hydrotreated reactor to be octanol (2-ethylhexanol) by adding hydrogen.

The hydroformylation reaction may be preformed in a continuous way, semi-continuous way or batch way, and the typical hydroformylation reaction is a gas or liquid recirculation system. It is important for the hydroformylation reaction to increase the reaction efficiency by smoothly contacting the starting materials that are composed of a liquid phase and gas phase. For this reason, conventionally the continuous stirred tank reactor (CSTR) that stirs for evenly contacting the components of liquid phase and gas phase inside the reactor was mainly used. In addition, U.S. Pat. No. 5,763,678 discloses the hydroformylation method, in which the circulation is used instead of the stirring by applying the reactor that is a type of loop. However, those methods have a limit to the improvement of the hydroformylation reaction efficiency and also single reactor cannot produce the satisfactory aldehyde product, so that the residence time of the reaction is made to be longer, or more than two reactors are connected in series thereby producing the product that has a required level.

In addition, the hydrogenation process of aldehydes generally uses the reactor, in which nickel-based or copper-based solid hydrogenation catalyst is filled inside the reactor. There are two ways for performing the reaction, such that the starting aldehydes are evaporated to perform the reaction in a vapor phase, or the starting aldehyes are introduced into the reactor as a liquid to perform the reaction in a liquid phase.

However, there is a problem that the selectivity of the reaction is reduced by generating an undesirable side reaction, such as esterification, acetal formation, etherification, and the like in the above reaction, even though the above catalysts types, the vapor phase, or the liquid phase are applied.

SUMMARY OF THE INVENTION

In order to solve the conventional technical problems as mentioned above, an object of the present invention provides an apparatus for producing alcohols from olefins, comprising a hydroformylation reactor that can improve the efficiency for producing aldehydes by increasing the contact surface between olefins of liquid phase and mixture gas of gas liquid and a hydrogenation reactor that can decrease a side reaction in the hydrogenation process of aldehydes, and a method for producing alcohols from olefins using the above apparatus.

As means for solving the above subjects, the present invention provides an apparatus for producing alcohols from olefins, comprising: a hydroformylation reactor comprising a spraying means for spraying olefins and a synthesis gas ($CO/H_2$) into a solution of catalyst mixture that is charged inside the reactor, in which the spraying means is installed at the upper part of the reactor; a reactor outlet for discharging the reaction mixture of the synthesis gas and olefins, in which the reactor outlet is located at the bottom part of the reactor; a distributor plate for changing the flow direction of olefins and the synthesis gas, in which the distributor plate is installed between the spraying means and the reactor outlet; and a circulation pipe for circulating the reaction mixture by recovering the reaction mixture from the reactor outlet and then supplying to the spraying means, in which the circulation pipe is connected to the reactor outlet and the spraying means;

a catalyst/aldehydes separator comprising a separation pipe for separating the reaction mixture from the circulation flow, in which the separation pipe is separated from any one of the circulation pipe; a catalyst/aldehydes separation machine for separating the catalyst mixture solution and aldehydes from the reaction mixture, in which the catalyst/aldehydes separation machine is connected to the separation pipe; a supplying pipe of the catalyst mixture solution for supplying the catalyst mixture solution to the circulation pipe, in which the supplying pipe is connected to any one of the circulation pipe and the catalyst/aldehydes separation machine; and an aldehyde recovering pipe for recovering aldehydes, in which the aldehyde recovering pipe is connected to the catalyst/aldehydes separation machine;

a hydrogenation reactor for adding hydrogen to the recovered aldehydes; and a distillation column comprising an inlet part for entering the hydrogenation reaction product passed through the hydrogenation reactor; a low boiling point component outlet part for discharging the low boiling point component among the hydrogenation reaction products; a middle boiling point component outlet part for discharging the meddle boiling point component among the hydrogenation reaction products; and a high boiling point component outlet part for discharging the high boiling point component among the hydrogenation reaction products.

As means for solving the above subjects, the present invention provides a method for producing alcohols from olefins comprising: hydroformlyating for obtaining aldehydes by forming a micro-bubble of olefins and the synthesis gas through spraying the synthesis gas ($CO/H_2$) and olefins in the catalyst mixture solution and reacting the micro-bubble and the catalyst mixture solution while changing the spraying flow of the synthesis gas ($CO/H_2$) and the olefins;

hydrogenating for obtaining the product of the hydrogenation reaction containing alcohols by adding hydrogen to aldehydes that are the product obtained from the above hydroformylation step; and separating the structural isomers of alcohols by using fractional distillation of the product obtained from the hydrogenation step.

The present invention relates to an apparatus for producing alcohols from olefins, comprising a hydroformylation reactor for producing aldehydes from olefins; a catalyst/aldehydes separator; a hydrogenation reactor for producing alcohols by hydrogenating the above aldehydes; and a distillation column.

Advantageous Effects

A hydroformylation reactor that is contained in an apparatus for producing alcohols from olefins according to the present invention provides a sufficient reaction area due to the broad contact surface of olefins and the synthesis gas that are a raw material for reaction by a distributor plate that is installed inside the hydroformylation reactor and a sufficient mixing between the raw materials and the reaction mixture according to the circulation of the reaction mixture so that the efficiency in term of production of aldehydes is excellent. In addition, the hydrogenation reactor for aldehydes suppresses sub-reactions to improve the efficiency in term of production of alcohols.

The apparatus for producing alcohols from olefins according to the present invention provides the improved process as mentioned above to save costs for producing alcohols from olefins and increase the efficiency in terms of production of alcohols.

The present invention was explained in details around the specific examples in the above sentence, but it can be understood by the person who has general information in the art that various modifications and variations can be possible within the range and the technical spirit of the present invention and those modifications and variations belong to the attached claims.

DESCRIPTION OF DRAWINGS

The above and other objects, features and advantages of the present invention will become apparent from the following description of preferred embodiments given in conjunction with the accompanying drawings, in which:

FIG. 1, (a) shown the making flow in outline showing the processes for producing alcohols from olefins according to an example of the present invention, and (b) shown the drawing showing the enlarged part of a venturi diffusion tube 122 that is composed of an inlet part 122a and a diffusion part 122b in the above (a) of FIG. 1.

Figure 2:
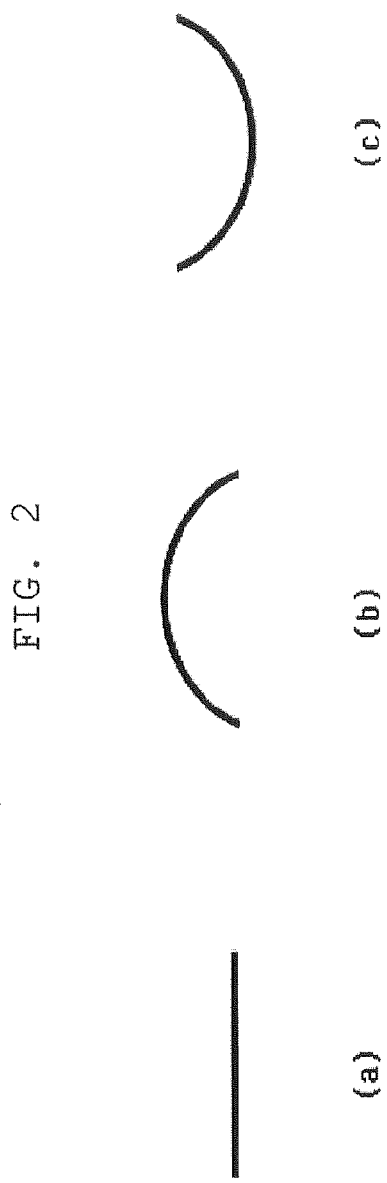
FIG. 2 is a sectional drawing of a distributor plate that is contained in a hydroformylation reactor of olefins according to the present invention.

EXPLANATIONS OF MARKS ABOUT MAIN PARTS OF FIGS.

100: Hydroformylation reaction apparatus
200: Catalyst/aldehydes separator
300: Hydrogenation reactor
400: Distillation column
500: Aldehyde distillation column
600: Aldol condensation reactor Best Modes for Carrying out the Invention Hereinafter, an apparatus for producing alcohols from olefins according to an example of the present invention will be described in detail with reference to accompanying drawings.

FIG. 1 shown the apparatus for producing alcohols from olefins according to an example of the present invention in outline.

The apparatus for producing alcohols from olefins according to an example of the present invention comprises: a hydroformylation reactor 100 comprising a spraying means 120 for spraying olefins and a synthesis gas ($CO/H_2$) into a solution of catalyst mixture that is charged inside the reactor, in which the spraying means is installed at the upper part of the reactor 100; a reactor outlet 130 for discharging the reaction mixture of the synthesis gas and olefins, in which the reactor outlet is located at the bottom part of the reactor; a distributor plate 140 for changing the flow direction of olefins and the synthesis gas, in which the distributor plate is installed between the spraying means and the reactor outlet; and a circulation pipe 150 for circulating the reaction mixture by recovering the reaction mixture from the reactor outlet and then supplying to the spraying means, in which the circulation pipe is connected to the reactor outlet and the spraying means;

a catalyst/aldehydes separator 200 comprising a separation pipe 210 for separating the reaction mixture from the circulation flow, in which the separation pipe is separated from any one of the circulation pipe 150; a catalyst/aldehydes separation machine 220 for separating the catalyst mixture solution and aldehydes from the reaction mixture, in which the catalyst/aldehydes separation machine is connected to the separation pipe 210; a supplying pipe 230 of the catalyst mixture solution for supplying the catalyst mixture solution to the circulation pipe, in which the supplying pipe is connected to any one of the circulation pipe and the catalyst/aldehydes separation machine; and an aldehyde recovering pipe 240 for recovering aldehydes, in which the aldehyde recovering pipe is connected to the catalyst/aldehydes separation machine;

a hydrogenation reactor 300 for adding hydrogen to the recovered aldehydes; and a distillation column 400 comprising an inlet part 410 for entering the hydrogenation reaction product passed through the hydrogenation reactor; a low boiling point component outlet part 420 for discharging the low boiling point component among the hydrogenation reaction products; a middle boiling point component outlet part 430 for discharging the meddle boiling point component among the hydrogenation reaction products; and a high boiling point component outlet part 440 for discharging the high boiling point component among the hydrogenation reaction products.

The more specific explanation about the hydroformylation reactor 100 is as follows.

The synthesis gas and olefins are sprayed in the catalyst mixture solution that is charged inside the reactor 110 by the spraying means 120 that is installed at the upper part of the reactor 100.

The spraying means 120 is not specifically limited if it can spray olefins and the synthesis gas in the catalyst mixture solution that is charged inside the reactor, and for example an ejector 121 installed with a nozzle can be used. The nozzle that is installed in the ejector 121 plays a role in increasing the speed by decreasing the distribution sectional area of olefins and the synthesis gas supplying inside the reactor in a high-pressure. The diameter of the nozzle may depend to the size of the reactor, and generally it is preferably 1 to 500 mm.

In addition, the ejector 121 is preferably combined with a venturi tube 122. The venturi tube 122 comprises the inlet part 122a that has a type of linear tube and a diffusion part 122b that has a tube type of expanding toward the bottom part, as shown in the figure. The inlet part 122a, in which olefins and the synthesis gas are flowing, is connected to the ejector 121 and the diameter of the inlet part 122a is the same with the diameter of the inlet of the diffusion part 122b and is smaller than that of the diffusion outlet. At the same time, the direction of the diffusion part 122b outlet is preferably toward the bottom of the reactor. The diameter of the inlet part is preferably 0.2 to 1000 mm, and the length of the diffusion inlet is preferably 1/50 to 1/2 of the whole length of the reactor. The diameter of the diffusion inlet is the same with that of the inlet part and the diameter of the diffusion outlet is preferably 1.0 to 10 times longer than the diameter of the diffusion inlet. In addition, the length of the diffusion part is preferably 0.1 to 10 times longer than that of the inlet part, and the whole length of the venturi tube combined with the inlet part and the diffusion part is preferably 0.01 to 0.95 times longer than that of the reactor body and most preferably 0.05 to 0.75 times.

The synthesis and olefins that are raw materials for reaction are sprayed inside the reactor via the ejector 121 and the venturi tube 122 that is connected to the ejector 121 and the sprayed olefins and the synthesis gas form micro-bubbles and are sprayed in the catalyst mixture solution that is charged inside the reactor. The micro-bubbles of olefins and the synthesis gas are contacted to the catalyst mixture solution so that the sufficient reaction area is provided due to the broad gas-liquid contact surface.

In addition, the flow of spraying of olefins and the synthesis gas is changed by the distributor plate 140 that is installed between the spraying means 120 and the reactor outlet 130. The residence time of the reaction raw materials in the reactor is increased due to the flow change of the reaction raw materials as mentioned above thereby improving the efficiency of the reaction. The flow change of the reaction raw materials is determined according to the location and shape of the distributor plate 140 so that the reaction efficiency can be modulated.

Figure 3:
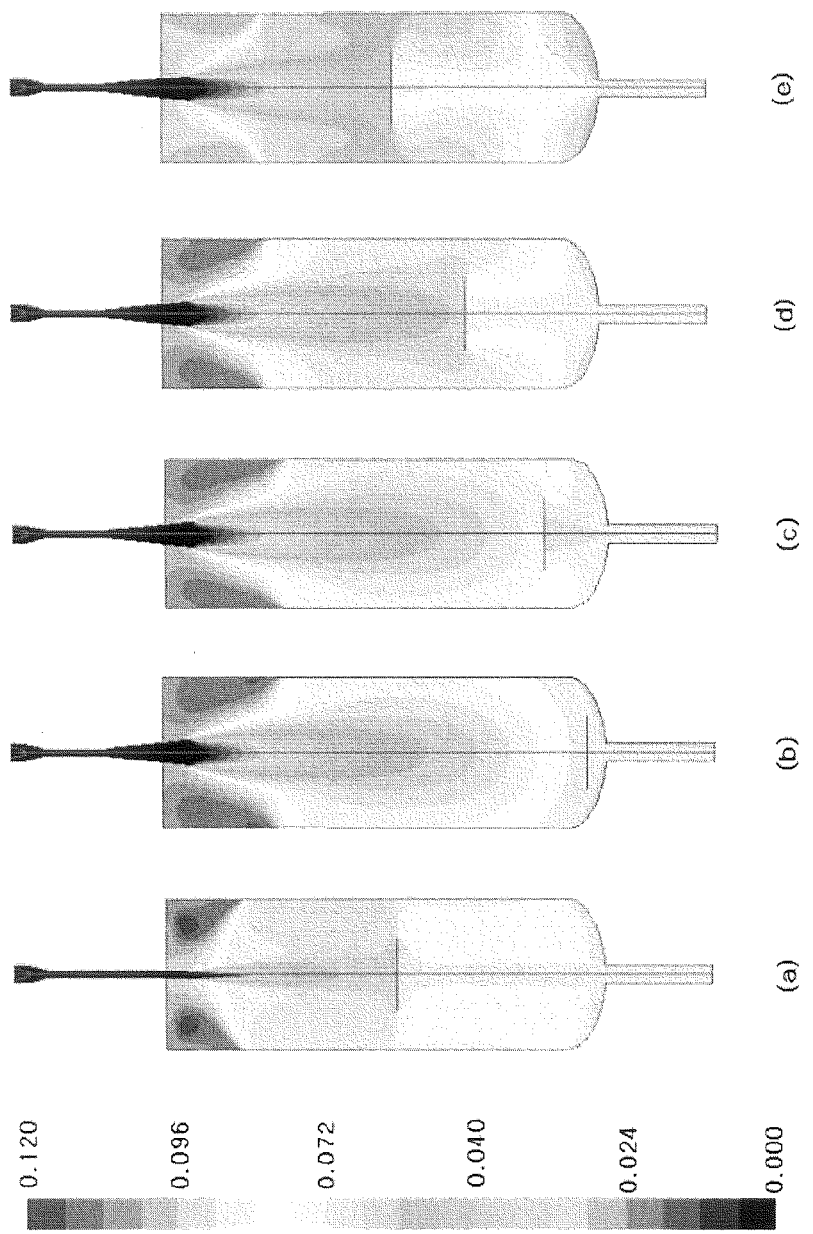
FIG. 3 and FIG. 4 are the results of process simulation of the hydroformylation reaction using the hydroformylation reactor according to the present invention, which show the reactivity according to the location of the distributor plate. X-axis in FIG. 4 is a radius of the bottom outlet tube and if the value of Y-axis (composition of product) is high, it means the quick reaction, relatively. (a) is when the flow rate of circulation is low, and (b)-(e) that have a high flow rate show that (e) is the highest.
Figure 4:
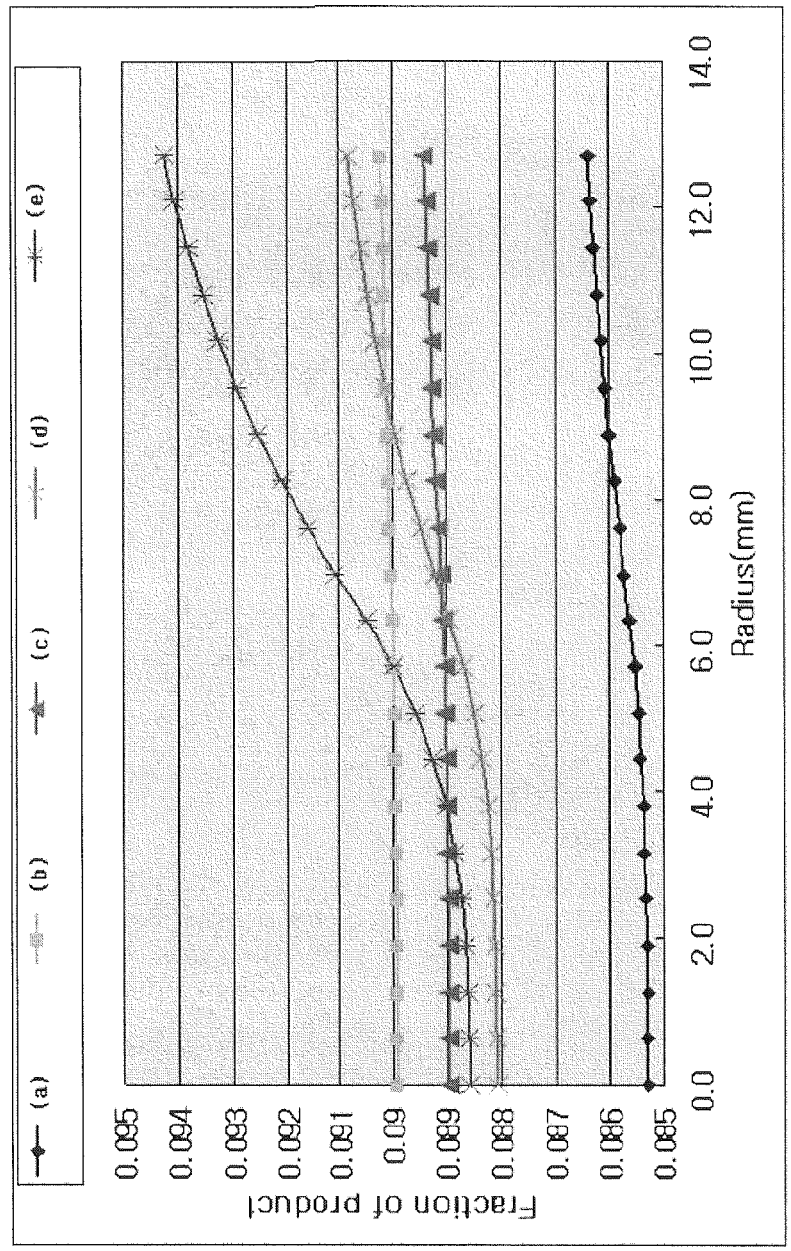

The distributor plate 140 is preferably located between 1/3 and 2/3 of the length up to the reactor outlet and venturi tube 122 outlet in a direction of the venturi tube from the reactor outlet 130, and most preferably 1/2. FIG. 3 and FIG. 4 that are attached show the reactivity according to the location of the distributor plate.

X-axis in the following FIG. 4 is a radius of the bottom outlet tube and if the value of Y-axis (composition of product) is high, it means the quick reaction, relatively. (a) in FIG. 4 is when the flow rate of circulation is low, and it can be shown that (b)-(e) having a high flow rate show (e) is the highest and the nearer the outlet, the higher the flow rate.

In addition, the shape of the distributor plate 140 can be a flat type, a convex type toward the direction of the diffusion tube, or a concave type, and preferably a concave type. FIG. 2 that is attached shown the sectional drawing of the distributor plate, in which (a) is a flat type, (b) is a convex type and (c) is a concave type.

The size of the distributor plate may be 10% to 75% of the diameter inside the reactor 100.

Figure 5:
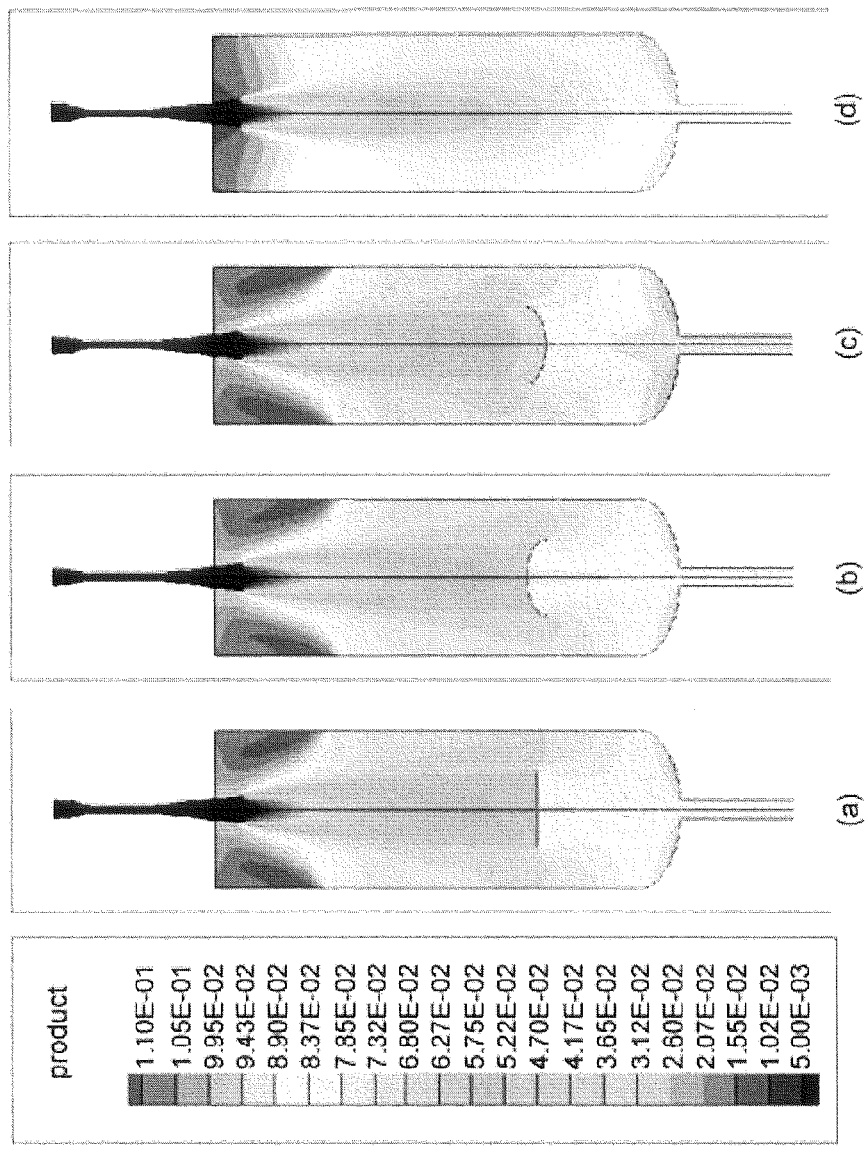
FIG. 5 and FIG. 6 are the results of process simulation of the hydroformylation reaction using the hydroformylation reaction apparatues according to the present invention, which show the reactivity according to the shape of the distributor plate.
Figure 6:
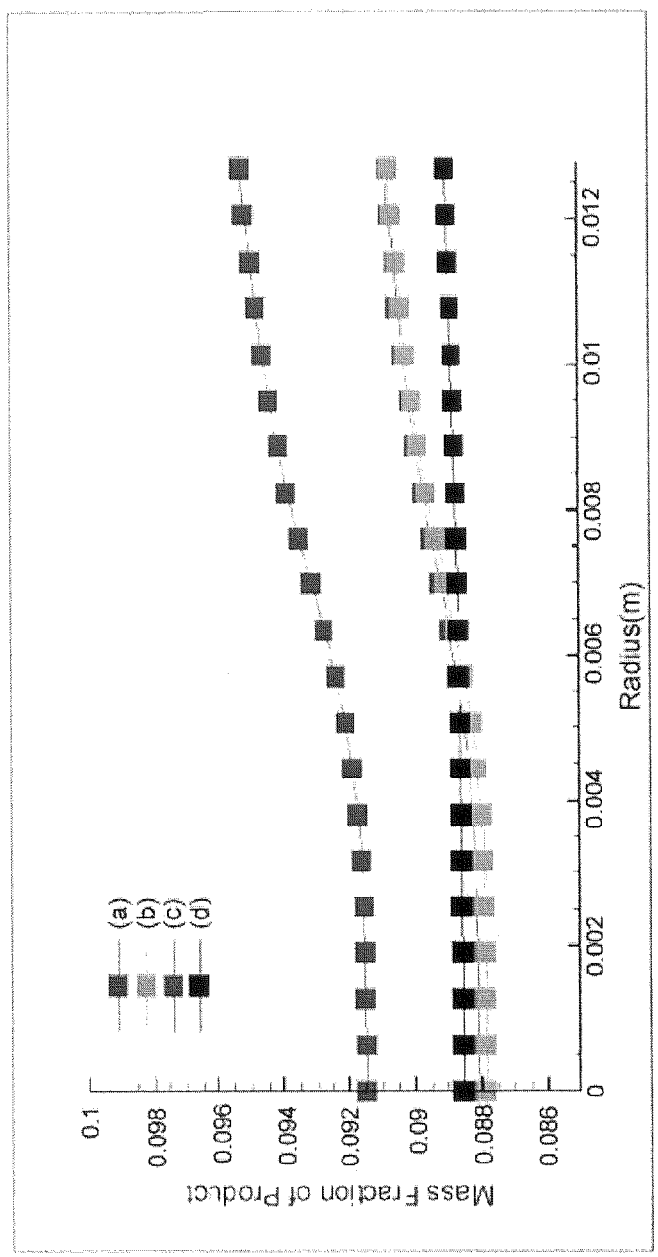

FIG. 5 and FIG. 6 that are attached show the reactivity according to the shape of the distributor plate. As shown in the following FIG. 6, it can be known that (c) is most favorable for the reactivity.

The hydroformylation reaction is progressed while spraying the synthesis gas and olefins inside the reactor as mentioned above, so that the reaction mixture containing the aldehydes, the catalyst mixture solution, non-changed olefins, the synthesis gas, other by-product of the reaction, and the like is presented inside the reactor. The reaction mixture is recovered at the bottom of the reactor by the circulation pipe 150 that is connected to the spraying means and the reactor outlet, and then supplied to the spraying means at the upper part of the reactor. The reaction mixture is sufficiently mixed with the reaction raw materials while spraying the reaction raw materials along with the reaction mixture due to the above circulation so that the efficiency of the reaction is improved. The circulation can be controlled by a circulation pump 160 that is installed in the circulation pipe.

In addition, the circulation pipe 150 may comprise a heat exchanger 170, and the heat exchanger is not limited to be located at the particular site on the circulation pipe. The heat exchanger 170 plays a role in maintaining the temperature of the reaction mixture that is suitable for the hydroformylation reaction condition.

The mixture that is separated from any one part of the circulation pipe of the hydroformylation reactor is separated into aldehydes and the catalyst mixture solution by the catalyst/aldehydes separator 200, and then the catalyst mixture solution is circulated to the reactor 110 and aldehydes is transferred to the aldehyde hydrogenation reactor 300.

Hereinafter, the catalyst/aldehydes separator 200 will be described in more details.

The catalyst/aldehydes separator 200 comprises a separation pipe 210 for separating the reaction mixture from the circulation flow, in which the separation pipe is separated from any one of the circulation pipe 150; a catalyst/aldehydes separation machine 220 for separating the catalyst mixture solution and aldehydes from the reaction mixture, in which the catalyst/aldehydes separation machine is connected to the separation pipe 210; a supplying pipe 230 of the catalyst mixture solution for supplying the catalyst mixture solution to the circulation pipe, in which the supplying pipe is connected to any one of the circulation pipe and the catalyst/aldehydes separation machine; and an aldehyde recovering pipe 240 for recovering aldehydes, in which the aldehyde recovering pipe is connected to the catalyst/aldehydes separation machine.

The reaction mixture of the hydroformylation reactor 100 is separated from any one part of the circulation pipe 150 by the separation pipe 210 in the catalyst/aldehyde separator and then supplied to the catalyst/aldehyde separation machine. The catalyst mixture solution that is separated from the catalyst/aldehyde separation machine 220 is circulated to the hydroformylation reactor through the catalyst mixture solution-supplying pipe 230 that is connected to any one part of the circulation pipe 150. The aldehydes that is separated from the catalyst/aldehydes separation machine 220 is transferred to the hydrogenation reactor through the aldehyde recovering pipe 240 that is connected to the catalyst/aldehyde separation machine.

The catalyst/aldehyde separation machine 220 is possible for separating the catalyst mixture solution and the aldehydes from the reaction mixture, and its type is not limited. For example, a gasifier, in which the aldehydes that are the low boiling point components among the reaction mixture is discharged in a vapor type and the catalyst mixture solution that is the high boiling point component is discharged in a liquid type, can be used.

The circulation of the catalyst mixture solution that not comprises aldehydes that are target materials can be continuously performed, and in some cases, a part of the reaction mixture that is circulated is discharged to reproduce the catalyst, or new catalyst solution or reactivated catalyst solution can be added to the circulation flow of the reaction mixture.

The aldehydes that are separated from the catalyst/aldehyde separator 200 are transferred to the hydrogenation reactor 300 and are changed to alcohols by the hydrogenation reaction.

The hydrogenation reactor 300 comprises a spraying means 312 for spraying the recovered aldehydes and hydrogen gas to the catalyst mixture solution that is charged inside the reactor 311; a reactor outlet 315 for discharging aldehydes and hydrogen gas, and the hydrogenated reaction mixture of aldehydes, in which the reactor outlet 315 is located at the bottom of the reactor; a circulation pipe 316 for circulating aldehydes and hydrogen gas, and the hydrogenated reaction mixture of aldehydes through recovering them from the reactor outlet and then supplying them to the spraying means, in which the circulation pipe is connected to the reactor outlet 315 and the spraying means 312. The hydrogenation reactor may comprise a loop reactor or dual fixed layers reactor.

The aldehydes and hydrogen gas, and the hydrogenated reaction mixture of aldehydes are sprayed in the catalyst mixture solution that is charged inside the reactor 311 by the spraying means 312.

The spraying means 312 may use an ejector 312 installing the nozzle. The nozzle that is installed in the ejector 312 plays a role in increasing the speed by decreasing the sectional area for spraying hydrogen gas and aldehydes that are supplied inside the reactor using a high-pressure.

The diameter of the nozzle may vary depending on the size of the reactor, and generally it is preferably 1 to 500 mm.

In addition, the ejector 312 is preferably combined with a venturi tube 314. The venturi tube 314 comprises the inlet part 314a and a diffusion part 314b as shown in the figure. The inlet part 314a is connected to the ejector 312 and the tube diameter of the inlet part 314a is the same with the diameter of the inlet of the diffusion part 314b and is smaller than that of the diffusion outlet. At the same time, the direction of the diffusion part 314b outlet is preferably toward the bottom of the reactor. The diameter of the inlet part is preferably 0.2 to 1000 mm and the diameter of the diffusion inlet is the same with that of the inlet part and the diameter of the diffusion outlet is preferably 1.0 to 10 times longer than the diameter of the diffusion inlet. In addition, the length of the diffusion part is preferably 0.1 to 100 times longer than that of the inlet part, and the whole length of the venturi tube combined with the inlet part and the diffusion part is preferably 0.01 to 0.95 times longer than that of the reactor body and most preferably 0.05 to 0.75 times.

The aldehydes and hydrogen gas, and the hydrogenated reaction mixture of aldehydes are sprayed inside the reactor via the ejector 312 and the venturi tube 314 that is connected to the ejector 312 and the sprayed olefins and the synthesis gas form micro-bubbles and are sprayed in the catalyst mixture solution that is charged inside the reactor. The micro-bubbles of olefins and the hydrogen gas are contacted to the catalyst mixture solution so that the sufficient reaction area is provided due to the broad gas-liquid contact surface so that the hydrogenation reaction efficiency is improved.

The aldehydes and hydrogen gas that are sprayed inside the reactor are reacted under presence of the catalyst mixture solution to produce alcohols that are the reaction products. Therefore, alcohols, aldehydes, hydrogen, reaction by-products and catalyst mixture solution are present inside the reactor, and the hydrogenation reaction mixture is recovered at the bottom part of the reactor and then supplied to the spraying means 312 at the upper part of the reactor by the circulation pipe 316 that is connected to the spraying means and the reactor outlet. The hydrogenation reaction mixture is sufficiently mixed with the reaction raw materials while spraying the reaction raw materials along with the reaction mixture due to the above circulation so that the efficiency of the reaction is improved. The circulation can be controlled by a circulation pump 317 that is installed in the circulation pipe 316.

In addition, the circulation pipe 316 may comprise a heat exchanger 318, and the heat exchanger is not limited to be located at the particular site on the circulation pipe. The heat exchanger 318 plays a role in maintaining the temperature of the reaction mixture that is suitable for the hydrogenation reaction condition.

The catalyst mixture solution that is charged inside the reactor 311 is a fluid containing nickel or copper, and then the explanation about the above fluid will be described later.

In addition, the hydrogenation reactor separates 319a the hydrogenation reaction mixture from any one part of the circulation pipe 316, separates into alcohols and the catalyst mixture solution in the catalyst mixture solution and alcohol separation machine 319, and circulates the separated catalyst mixture solution to the hydrogenation reactor 311 through the catalyst mixture solution supplying pipe 319b that is connected to any one part of the circulation pipe 316, and then the hydrogenation reaction mixture containing alcohols may be transferred to the distillation column.

Figure 7:
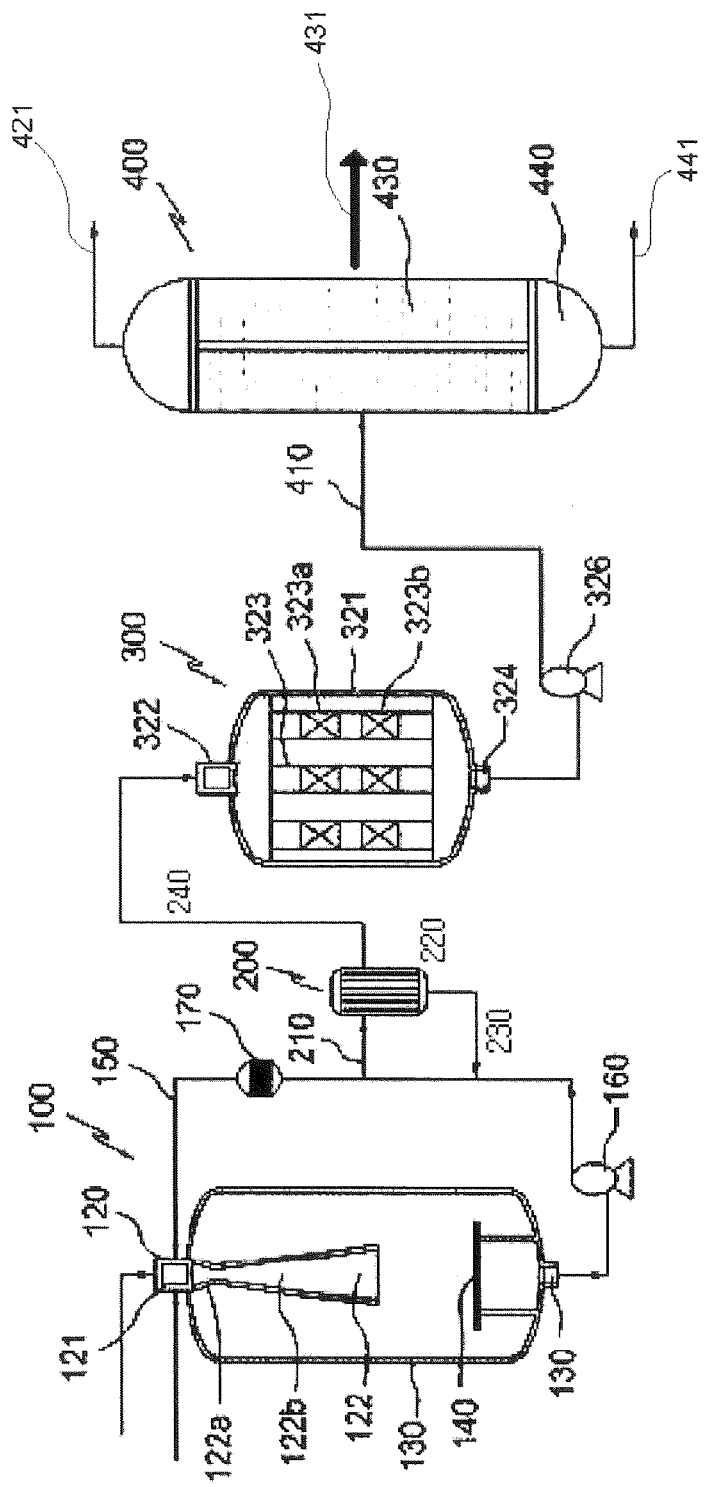
FIG. 7 shown the making flow in outline showing the processes for producing alcohols from olefins according to an example of the present invention.

In addition, as shown in the attached FIG. 7, the hydrogenation reactor 300 may be composed of a spraying means 322 for spraying the recovered aldehydes and hydrogen gas inside the reactor 321; a nickel catalyst layer 323a having a high activity, in which the nickel catalyst layer is located at the site of flowing aldehydes and hydrogen; a copper catalyst layer 323b having a low activity, in which the copper catalyst layer is located after the nickel catalyst layer; and a reactor outlet 324 for discharging the hydrogenation reaction mixture, in which the reactor outlet is located after the copper catalyst layer.

The hydrogen gas and the aldehydes are sprayed inside the reactor 321 by the spraying means 322. The sprayed aldehydes and hydrogen gas are passed through the nickel catalyst layer 323a having a high activity and the copper catalyst layer 323b having a low activity in order, and then alcohols are produced by adding hydrogen to the aldehydes during passing.

The hydrogenation reaction of aldehydes generally use a single catalyst, such as nickel or copper, but the present invention is characterized of using dual layers catalysts 323 composing nickel and copper. Generally, when using the nickel catalyst having a high activity, sub-reactions may be generated by increasing the temperature at the reactor outlet because the temperature is increased according to the exothermic reaction. There is a problem due to the sub-reactions, rather than the increase of the reaction efficiency due to the catalyst having a high activity. Therefore, the present invention is characterized by increasing the reaction speed of the reactor inlet having a high concentration of the reactants that should be changed through using the nickel catalyst 323a having a high activity and by suppressing the sub-reactions through using the copper catalyst layer 323b having a low activity at the reactor outlet having a low concentration of the reactants that should be changed.

The hydrogen gas and aldehydes that are sprayed inside the reactor are passed through dual catalysts layers to produce alcohols that are the reaction products. The hydrogenation reaction product containing alcohols that is passed through the hydrogenation reactor 300 is transferred to the distillation column 400.

The distillation column 400 comprising an inlet part 410 for entering the hydrogenation reaction product passed through the hydrogenation reactor; a low boiling point component outlet part 420 for discharging the low boiling point component among the hydrogenation reaction products; a middle boiling point component outlet part 430 for discharging the meddle boiling point component among the hydrogenation reaction products; and a high boiling point component outlet part 440 for discharging the high boiling point component among the hydrogenation reaction products.

Each inlet part and outlet part of the distillation column are divided by a divided wall, and the divided wall is designed to insulate so that the temperature and pressure in each inlet part and the outlet part are individually controlled. The hydrogenation reaction product passed through the hydrogenation reactor comprises alcohols, aldehydes, hydrogen, the reaction by-products, and the like, and each material is fractionally distilled according to the boiling point.

The inlet part is preferably driven at 20 to 100° C. and 1.0 to 5.0 par of pressure. Normal/iso-aldehydes, water, iso-alcohol, and the like that are the low boiling point components among the hydrogenation reaction products in the inlet part are vaporized and then transferred to the low boiling point component outlet part 420, and discharged through the low boiling point component outlet tube 421. The low boiling point component outlet part 420 is preferably driven at 30 to 120° C. and 1.0 to 5.0 par of pressure. The middle boiling point components that are not vaporized in the inlet part and the low boiling point outlet part 420 are transferred to the middle boiling point component outlet part 430, and then discharged through the middle boiling point component outlet tube 431. The main component in the middle boiling point components among the hydrogenation reaction products is normal-alcohol and iso-alcohol mixture. The middle boiling point component outlet part 430 is preferably driven at 40 to 170° C. and 0.01 to 5.0 par of pressure. In addition, the high boiling point components that are not vaporized in the middle boiling point outlet part are transferred to the high boiling point component outlet part 440, and then discharged through the high boiling point component outlet tube 441. The main component in the high boiling point components among the hydrogenation reaction products is normal-alcohol, aldehyde dimer, aldehyde trimer, and the like. The high boiling point component outlet part 440 is preferably driven at 60 to 250° C. and 0.1 to 5.0 par of pressure.

Figure 8:
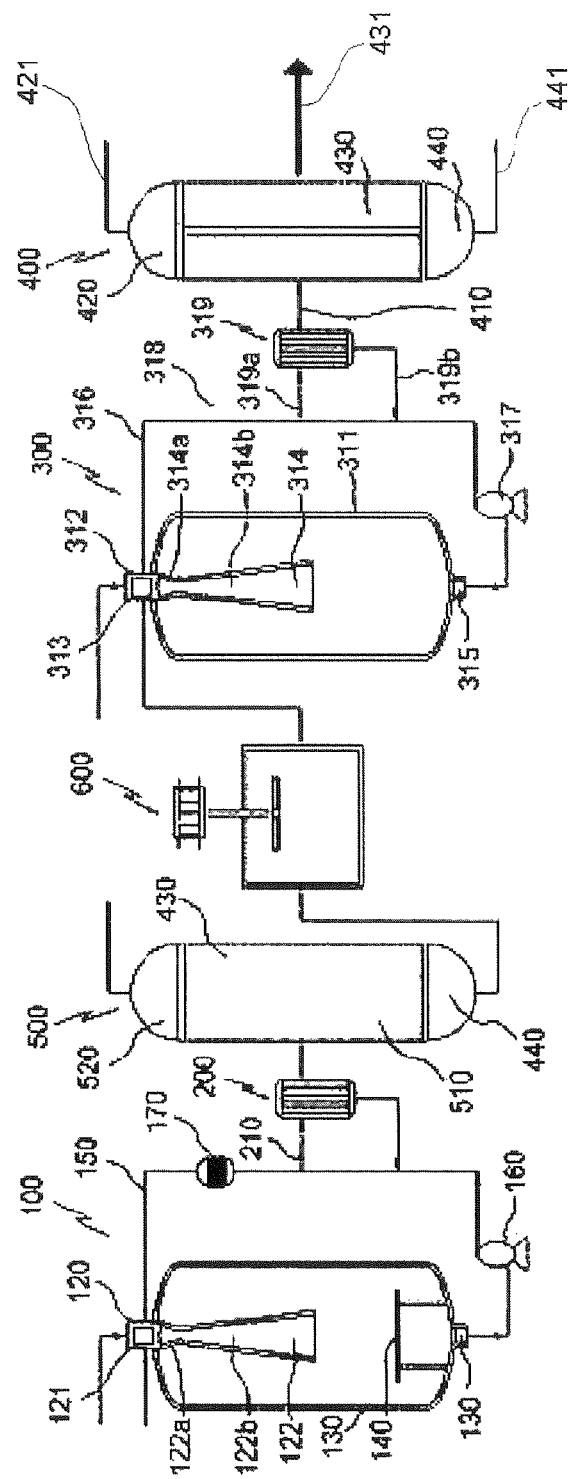
FIG. 8 shown the making flow in outline showing the processes for producing alcohols from olefins according to an example of the present invention.

As shown in the attached FIG. 8, the apparatus for producing alcohols from olefins may further comprise a distillation column 500 for separating aldehdyes into normal-aldehydes and iso-aldehydes after the hydroformylation reactor; and an aldol condensation reactor 600 for producing aldehydes having increased carbon number by the aldol condensation of the normal-aldehydes.

The aldol condensation reactor may be connected to the hydrogenation reactor that produces alcohols by adding hydrogen to the aldehydes having the increased carbon number that are recovered from the aldol condensation reactor.

When further comprising the distillation column 500; and the aldol condensation reactor 600, the alcohols, in which the carbon number has increased two times rather than that of the aldehydes produced after the hydroformylation reactor, can be produced.

For example, when processing the hydroformylation reaction with propylene, the normal-butylaldehydes and iso-butylaldehydes are produced and 2-ethylhexanal is produced by the aldol condensation. The hydrogenation reaction can be performed using the aldehydes having the increased carbon number to produce octanol (2-ethylhexanol).

The present invention also relates to a method for producing alcohols from olefins comprising: hydroformlyating for obtaining aldehydes by performing the reaction while spraying olefins and the synthesis gas ($CO/H_2$) in the catalyst mixture solution and changing the spraying flow of the synthesis gas and olefins;

hydrogenating for obtaining the product of the hydrogenation reaction containing alcohols by adding hydrogen to aldehydes that are the product obtained from the above hydroformylation step; and separating the structural isomers of alcohols by using fractional distillation of the product obtained from the hydrogenation step.

The hydroformylation step is to obtain aldehydes by forming micro-bubbles of olefins and the synthesis gas through spraying olefins and the synthesis gas ($CO/H_2$) in the catalyst mixture solution and than reacting the catalyst mixture solution and micro-bubbles while changing the spraying flow of the olefins and the synthesis gas.

The micro-bubbles are formed while spraying olefins and the synthesis gas and are contacted with the catalyst mixture solution so that the sufficient reaction area is provided due to the broad gas-liquid contact surface. In addition, since the reaction is performed while changing the spraying flow of the olefins and the synthesis gas, the residence time of the reaction raw materials is longer in the reactor so that the efficiency of the reaction is improved.

The hydroformylation step is preferably performed using the hydroformylation reactor as mentioned above.

The catalyst mixture solution in the hydroformylation step is generally used in the hydroformylation reaction and may comprise the transition metal catalyst and ligand.

The transitions metal catalyst can be used without any limitation if it is typically used in the art, and for example the catalysts having the transition metal, such as cobalt (Co), rhodium (Rh), iridium (Ir), ruthenium (Ru), osmium (Os), platinum (Pt), palladium (Pd), iron (Fe) or nickel (Ni), and the like as a metal center, can be used. Specifically, more than one of complex catalyst selected from the group consisting of cobaltcarbonyl [$Co_2(CO)_8$], acetylacetonatodicarbonylrhodium [Rh(AcAc)(CO)$_2$], acetylacetonatocarbonyltriphenylphosphinerhodium [Rh(AcAc)(CO)(TPP)], hydridocarbonyltri(triphenylphosphine)rhodium [HRh(CO)(TPP)$_3$], acetylacetonatodicarbonyliridium [Ir(AcAc)(CO)$_2$] and hydridocarbonyltri(triphenylphosphine)iridium [Hir(CO)(TPP)$_3$] can be used.

In addition, tri-substituted phosphine, phosphine oxide, amine, amide, isonitrile, and the like can be used as the ligand, and the tri-substituted phosphine is preferably used. The tri-substituted phosphine comprises triaryl phosphine, triarylphosphate, alkyldiarylphosphine, and the like, but is not limited thereto. More specifically, triphenylphosphine, tritolylphosphine, tirphenylphosphate, n-butyldiphenylphosphine, and the like can be used as the tri-substituted phosphine.

The solvent used in the catalyst mixture solution comprises for example, aldehyde type, such as propane aldehyde, butyl aldehyde, pentyl aldehyde, valer aldehyde, and the like; ketone type, such as acetone, methyl ethyl ketone, methyl isobutyl ketone, acetophenone, cyclohexanon, and the like; alcohol type, such as ethanol, pentanol, octanol, thensanol, and the like; aromatic type, such as benzene, toluene, xylene, and the like; ether type, such as tetrahydrofuran, dimethoxyethane, dioxane, and the like; and paraffin hydrocarbon, such as heptane, and the like can be used, but is not limited thereto. Preferably, propane aldehyde, butyl aldehyde, pentyl aldehyde, valer aldehyde, and the like that are the reaction products are used. In addition, for the concentration of the catalyst mixture solution, the relevant solvent weight is preferably 30% to 99% proportion of the whole solvent weight.

The olefin of carbon number 2 to 20 can be used as the olefins used in the present invention, but not limit thereto. More specifically, it comprises ethylene, propylene, 1-butene, 1-pentene, 1-hexane, 1-heptane, 1-octene, 1-nonene, 1-decene, 1-undecene, 1-tridecene, 1-tetradecene, 1-pentadecene, 1-hexadecene, 1-heptadecene, 1-octadecene, 1-nonadecene, 1-eicocene, 2-butene, 2-methylpropene, 2-pentene, 2-methylbutene, 2-hexane, 2-heptane, 2-ethylhexane, 2-octene, styrene, 3-phenyl-1-propene, 4-isopropylstyrene, and the like, and most preferably ethylene, propylene, 1-butene, 2-butene, 1-pentene, 2-pentene, 2-methylbutene, and the like.

The synthesis gas that is another starting material of the hydroformylation reaction is the mixture gas of hydrogen and carbon monoxide, and the mixture proportion of $CO:H_2$ is preferably 5:95 to 70:30, more preferably 40:60 to 60:40 and most preferably 45:55 to 55:45, but not limited thereto.

The mole ratio of the olefin and the synthesis gas is preferable 95:5 to 5:95, and most preferably 75:25 to 25:75.

In addition, the olefin and the synthesis gas are preferably spraying in 5 to 200 bar of pressure, respectively. In addition, the linear speed for spraying the olefins and the synthesis gas is preferably 1 m/sec to 50 m/sec, and more preferably 5 m/sec to 30 m/sec. The pressure difference between before and after passing the catalyst mixture solution through the spraying means is preferably 0.1 bar to 10 bar and more preferably 0.5 bar to 5 bar.

The reaction is preferably performed at 50 to 200° C. and more preferably 50 to 150° C. of the temperature. In addition, the reaction is preferably performed at 5 to 100 bar, and more preferably at 5 to 50 bar of the pressure.

In addition, preferably the hydroformylation step further comprises the circulation step of the reaction mixture that is supplied into the catalyst mixture solution along with the olefins and the synthesis gas by recovering the reaction mixture.

The reaction mixture that is discharged through the reactor outlet is recovered, and is sufficiently mixed with the reaction raw materials by the circulation system that is supplied inside the reactor, so that the efficiency of the reaction is improved. The reaction mixture comprises the non-changed olefins, the reaction by-products, the catalyst mixture solution, and the like, in addition to aldehydes (Normal- and iso-butylaldehydes) that is target material.

The circulation system can be achieved by the circulation tube and the circulation pump that is connected to the circulation tube, in which the circulation tube is combined with the spraying means of the reactor and the reactor outlet. The flowing amount of the circulated reaction mixture is preferably 0.01 to 20 times larger than the volume that is charged in the reactor per a minute.

In addition, the hydroformylation step may further comprise recovering aldehydes, in which the part of the circulated reaction mixture is separated; the aldehydes and the catalyst mixture solution are separated from the separated part of the circulated reaction mixture; the separated catalyst mixture solution is supplied to the circulation flow to recover the aldehydes.

Specifically, when the olefin that is the starting material of the hydroformylation method is propylene, the reaction mixture comprises butyl aldehydes, more specifically, normal-butylaldehydes and iso-butylaldehydes; the reaction mixture is transferred to the catalyst/aldehyde separation machine to separate into aldedydes and the catalyst mixture; and then the catalyst mixture is circulated to the reactor and the aldehyde component is transferred to the hydrogenation step.

The hydrogenation step is the step for obtaining the hydrogenation reaction product containing alcohols by adding hydrogen to aldehydes that is the product. The method for hydrogenating aldehdyes can use the method that is generally used in the art, but it is preferably performed as follows:

The hydrogenation step is performed by forming micro-bubbles of hydrogen gas and aldehydes through spraying the recovered hydrogen gas and aldehydes in the catalyst mixture solution and reacting the micro-bubbles and the catalyst mixture solution.

The catalyst mixture solution preferably comprises Raney-Ni or copper powder. The catalyst mixture can use solvent and aldehyde or alcohol can be sued as the proper solvent. Specifically, if the olefin that is the starting material in the hydroformylation method is propylene and hence the material that is injected in the hydrogenation reactor is butylaldehyde, normal- or iso-butylalcohol is preferable as solvent. The composition of the relevant solvent is preferably 2% to 99% based on the weight ratio, and more preferably 20% to 90%.

In addition, the hydrogenation method of aldehydes is preferably performed by passing the recovered aldehyde and hydrogen gas through the catalyst layer that is composed of double layers, such as Ni catalyst layer having a high activity and Cu catalyst layer having a low activity.

Generally the hydrogenation reaction of aldehydes use a single catalyst, such as nickel or copper, but the present invention is characterized by using the catalyst layer that is composed of double layers, such as nickel and copper. The catalyst layer that is composed of the double layers is in a fixed phase and aldehydes and hydrogen gas in a fluid phase are passed through the above double catalyst layers.

Generally, when using only nickel catalyst, sub-reactions may be generated by increasing the temperature at the reactor outlet because the temperature is increased according to the exothermic reaction. There is a problem due to the sub-reactions, rather than the increase of the reaction efficiency due to the catalyst having a high activity.

Therefore, the present invention is characterized by increasing the reaction speed of the reactor inlet having a high concentration of the reactants that should be changed through using the nickel catalyst having a high activity and by suppressing the sub-reactions through using the copper catalyst layer having a low activity at the reactor outlet having a low concentration of the reactants that should be changed.

The aldehydes in the hydrogenation step preferably comprises more than one of aldehydes and 1 to 20 carbons due to the hydroformylation reaction of olefins, but is not limited thereto. For example, there are formaldehyde, acetaldehyde, propionaldehyde, n-butylaldehyde, iso-butylaldehyde, n-valeraldehyde, iso-valeraldehyde, n-hexaaldehyde, n-heptaaldehyde, n-octanal, 2-ethylhexanal, 2-ethylhexenal, n-decanal, 2-ethylbutanal, propargylaldehyde, acrolein, glyoxal, crotonaldehyde, furfural, aldol, hexahydrobenzaldehyde, alpha-citronellal, citral, chloral, trimethylacetaldehyde, diethylacetaldehyde, tetrahydrofurfural, phenylaldehyde, cinnamaldehyde, hydrocinnamaldehyde, and the like. Propionaldehyde, n-butylaldehyde and iso-butylaldehyde, n-valeraldehyde and iso-valeraldedhye are preferable.

For example, when the hydroformylation reaction is performed by using propylene, normal-butylaldehyde and iso-butylaldehyde are produced and normal-butylalcohol and iso-butylalcohol can be produced by performing the hydrogenation step.

The aldehydes are preferably sprayed at 0.1 to 100 m/sec of the speed. While the aldehydes are sprayed at the certain speed, the hydrogen gas is drew inside the hydrogenation reactor.

The mole ratio of the aldehydes and the hydrogen gas is preferably 1:10 to 10:1. Preferably, the reaction temperature is 50 to 300° C. and the reaction pressure is 2 to 100 bar.

The separation step is to separate the structural isomer of alcohol by the fractional distillation of the hydrogenation reaction product that is the product from the hydrogenation step.

The hydrogenation reaction product comprises aldehydes, hydrogen, and reaction by-products, in addition to alcohols that are target material. The method for separating the alcohols that are target material can use the method that is generally used in the art, but preferably uses the following method.

The hydrogenation reaction product can be distillated by using the column having the divided regions by a divided wall. The divided wall is designed to be insulated, and the temperature and the pressure of each divided region can be individually different from the temperature and the pressure of driving the conventional column that is generally used according to the location and the site of the divided region and also can be properly modulated according to the plan. The hydrogenation reaction product is fractionally distillated according to the boiling point while passing through each divided region. The normal- and iso-aldehyde, water, iso-alcohol, and the like that are the low boiling point component among the hydrogenation reaction products are vaporized in the divided region that can be modulated to be relative lower temperature and pressure to discharge to the upper part of the column. In addition, the iso-alcohol and normal-alcohol that are the middle boiling point component are not vaporized or are liquefied during the vaporization to discharge in the section of the column middle boiling point. In addition, the very small amount of the high boiling point component, such as the normal-alcohol, aldehyde dimer, aldehyde trimer, and the like is not vaporized and discharged in a liquid phase through the bottom part of the column.

For example, when the hydroformylation reaction is performed by using propylene, the normal-butylaldehyde and the iso-butylaldehyde are produced, and the normal-butylalcohol and the iso-butylalcohol are obtained as the final material by performing the hydrogenation step and distillation purification step.

The aldol condensation step may be further comprised to obtain aldehydes having an increased carbon number by the aldol condensation of aldehydes recovered from the hydroformylation step. That is, the separation step for separating aldehydes that is the product from the hydroformylation step into normal-aldehyde and iso-aldehyde; and the aldol condensation step for obtaining aldehyde having an increased carbon number by the aldol condensation of the normal-aldehyde are further performed after the hydroformylation step so that the hydrogenation step can be performed by using the aldehydes having an increased carbon number. When further performing the above steps, the alcohols having an increased carbon number can be produced.

For example, when the hydroformylation reaction is performed by using propylene, the normal-butylaldehyde and iso-butylaldehyde are produced and 2-ethylhexanal is produced by the aldol condensation. The hydrogenation step may be performed by using the aldehydes having an increased carbon number to produce octanol (2-ethylhexanol).

Hereinafter, the present invention will be described in more detail through Examples and Comparative Examples, but it is only for helping the understanding of the present invention and the range of the present invention will not be limited thereto.

EXAMPLE

Example 1.1

Preparation of Catalyst Solution 3.2 kg of triphenylphosphine was added to 28.7 kg of normal-butylaldehyde having 99% purity and then completely dissolved. 45.9 kg of acetylacetonatodicarbonyl triphenylphosphine Rhodium (ROPAC) catalyst was further added to prepare 32 kg of catalyst solution.

Example 1.2

Step for Producing Aldehyde

Two loop reactors having 30 liter of volume were prepared, and the nozzle having 5 mm of diameter and the venturi diffusion tube were installed at the head part of each loop reactor, in which for the venturi diffusion tube, the diameter of the diffusion tube inlet was 10 mm, the diameter of the diffusion tube outlet was 20 mm and the length of the diffusion tube was 30 cm. In addition, the distributor plate having a flat shape and 70 mm diameter was fixed at 200 mm point from the bottom outlet in the reactor. The circulation pump was installed at the outside of the reactor to circulate the reaction solution in a flow speed of 20 liter per 1 minute to the nozzle in each reactor head, and the heat exchanger was installed at the outside circulation line in all of two reactors to remove heat of the reaction according to the reaction.

Two reactors were connected in series, and one of the circulation lines in an preceding reactor that was a first reactor among two reactors connected in series was connected to the upper part of the following reactor and a controller was installed so that the preceding reactor can be continuously driven on the certain liquid level.

Like the preceding reactor, one of the circulation lines in the following reactor that was a second reactor connected to the preceding reactor in series supplies the reaction mixture to the evaporator for separating aldehydes, and then the controller was installed so that the following reactor can be continuously driven on the certain liquid level.

Propylene and the synthesis gas that are the raw materials were individually supplied to each loop reactor that is connected in series. As the reaction goes, the separated and recovered aldehydes that was entered from the following reactor to the evaporator was injected to the hydrogenation reactor along with hydrogen gas via a condenser, and the remaining reaction catalyst solution after aldehydes was recovered through the evaporator was again circulated to the preceding reactor via a special pump. 16 kg of the above prepared catalyst solution was charged in two reactor, respectively, and nitrogen gas and propylene were purged each two times, and then the reaction temperature was maintained at 89° C. through the circulation pump 160 and the heat exchanger 170. When the temperature inside the reactor was stabilized, propylene was injected until the pressure inside each reactor became 12 bar.

Since then, after the temperature and the pressure were stabilized, propylene that is the raw material was supplied in a flow rate of 3.7 kg/hr to the preceding reactor and the synthesis gas was supplied in a flow rate of average 2.2 kg and 0.5 kg per 1 hour to the preceding reactor and the following reactor. The liquid level of each reactor was maintained at 20 liter. After the temperature and the pressure of the preceding reactor and the temperature and the pressure of the following reactor were stabilized and then reached to the normal state, i.e., 18 barg and 89° C. in the preceding reactor and 15 barg and 89° C. in the following reactor, the continuous driving was performed for 240 hours.

As a result, the condensed component from the evaporator was analyzed and the production amount of butylaldehydes was measured. It could be known that total 1,512 kg of butylaldehydes was produced, which means that 6.3 kg of butylaldehydes was produced per 1 hour. The conversion efficiency was 99.3%, in which the conversion efficiency means the conversion rate from the injected propylene to butylaldehydes, not from the injected propylene to propane.

Example 1.3

Step for Hydrogenating Aldehydes

Example 1.3.1

Hydrogenation of Aldehydes Using Loop Reactor

As a next step, total weight 16 kg of catalyst solution prepared by mixing 100% normal-butylalcohol and 2.4 kg of slurry Raney-nickel catalyst was charged in the loop reactor having the same structure and volume as mentioned above; nitrogen was purged each two times; and then the reaction temperature and pressure were maintained at 110° C. and 25 bar through the circulation pump 317 and the heat exchanger 318, respectively; and the liquid level was set at 80% level through the controller. When the temperature was stabilized, while the flow rate of the circulation pump was maintained at liter per 1 hour; as mentioned above Example 1.2, the produced butyl aldehydes was supplied in a speed of 6.3 kg per 1 hour to the reactor along with hydrogen gas of 0.35 kg per 1 hour. The total weight of the hydrogenation reaction product having the butyl alcohol as a main component was 587 kg, which means average 6.52 kg per 1 hour, in which the butyl alcohol was produced from the result of continuous driving for 90 hours after reaching to the normal state while the liquid lever was maintained.

As shown in the results of analyzing the components through gaschromatograpy, the normal-butylalcohol was 86.9%, the iso-butylalcohol was 8.7%, a heavy component, such as the butylaldehyde trimer was 4.2%, and water was 0.2% as weight ratio.

Example 1.3.2

Hydrogenation Step of Aldehydes using Dual Fixed layers Catalyst Reactor

As shown in FIG. 7, a nickel catalyst that was put into gamma-alumina was charged up to 210 cm from the upper 10 cm of the reactor having a column type, of which the diameter was 8 cm and the length was 330 cm; alumina balls were filled up to 230 cm of deep from that; and then the copper catalyst that was put into the gamma-alumina was filled up to the relevant length, i.e., 320 cm from that. While the temperature of the reactor outlet was maintained not over 110° C. using the special circulation pump and the outside heat exchanger, the pressure inside the reactor was maintained at bar. The normal-butylalcohol was used as the solvent medium for the reaction and the heat exchange, and the flow amount of the circulation was maintained in 38 kg per 1 hour. After reaching the normal state, the driving was performed for 90 hours, and the total weight of the hydrogenation reaction product having butylalcohol as a main component was 581 kg, which means average 6.45 kg per 1 hour.

As shown in the results of analyzing the components through gas chromatography, the normal-butylalcohol was 87.1%, the iso-butylalcohol was 8.6%, a heavy component, such as the butylaldehyde trimer was 4.3%, and water was 0.2% as weight ratio.

Example 1.4

Alcohol Purification Step Using DWC (Divided Wall Column)

DWC (Divided Wall Column) was prepared by blocking and equally dividing in a vertical in the pipe by using a metal separate membrane inside the pipe except each 10 cm of both ends of pipe using the pipe, of which the diameter was 8 cm and the length was 94 cm. The packed column having 18 plates of theoretical plate number was constructed by using an rasping ring, of which the average diameter was 1 cm and a glass wool to the pre column that was flowed with Feed based on the process simulation results, and also was constructed by using a main column, in which the middle boiling point outlet was toward the main column, as the same way. The packed column having 6 plates of theoretical plate number was constructed as the same way at both parts of the upper part of the column installing the condenser and the bottom part of the column installing a reboiler. Therefore, the pre column side Feed inlet part was 18 plates and the main column side the middle boiling point outlet was 30 plates. As mentioned above Example 1.3, while the hydrogenation reaction product was supplied at a flow rate of 6.4 kg per 1 hour to 6th plate of the pre column via the startup and stabilization step, the middle boiling point component was continuously recovered from 12nd plate from the upper part of the main column, the upper part and the bottom part of the column. The driving time of whole normal state was 86 hours, total 1.07 kg of water and less than 20 g of iso-butylalcohol were obtained at the upper part of the column.

A tri-component mixture containing 47.7 kg of iso-butylalcohol, 476.6 kg of the normal-butylalcohol, and less than 5 g of water was obtained through the middle boiling point outlet. 23 kg of aldehyde trimer and less than 0.5 kg of the normal-butylalcohol were obtained from the bottom part of the column. The energy amount that was supplied from the reboiler to the column under the driving condition of the normal state was average 1.49 MCal per 1 hour when exchanging.

Example 2

Preparation of Alcohol having Increased Carbon Number through Aldol Condensation Reaction

Example 2.1

Preparation of aldehyde having Increased Carbon Number through Aldol Condensation Reaction 20 liter of liquid that was mixed with 1:2 ratio of 2.0% NaOH aqueous solution and normal-butylaldehyde was charged in the continuous stirred-type reactor (CSTR) of 30 liter vertical tank-type, and then the temperature was maintained at 120° C. and the pressure was maintained at 5 barg in the reactor.

While the stirring rotation number was maintained at 300 RPM, 240 kg of the normal-butylaldehydes having 99% purity as Feed for the aldol condensation reaction were obtained through the fractional distillation with the aldehyde mixture produced from the above Example 1.3. The resulted normal-butylaldehydes were continuously injected in 6.3 kg per 1 hour; and while the liquid level was maintained at 20 liter, the reaction products were recovered through a decanter for 32 hours under the driving condition of the normal state.

The total weight of reaction products was 158 kg; as shown in the analysis result, ethylpropylacrolein was 96%, normal-butyl aldedhyde was 3.9% and aldehyde trimer was 0.1%, which means that average 4.74 kg of ethylpropylacrolein was produced per 1 hour.

Example 2.2

Preparation of Alcohol having Increased Carbon number through Hydrogenation

The hydrogenation reaction was performed by using the loop reactor with the same method to Example 1.3.1 except supplying 96% ethylpropylacrolein reaction product produced from Example 2.1 in a rate of average 4.7 kg per 1 hour, along with hydrogen in a rate of 0.26 kg per 1 hour.

While the liquid level was maintained, after reaching the normal state, the driving was continuously performed for 28 hours thereby obtaining 136 kg of the total weight of the hydrogenation reaction product having octanol as a main component in a rate of average 4.86 kg per 1 hour.

From analyzing the components through the gas chromatography, butanol was 0.5%, octanol was 96%, a heavy component, such as butylaldehyde trimer, was 3.3%, and water was 0.2%.

Comparative Example 1

The driving was continuously performed for 72 hours with the same method to Example 1.2, except using two continuous stirred-type reactor (CSTR) of 30 liter vertical tank-type, in which the reactors were connected in series. As a result, 436 kg of the total amount of butylaldehydes was produced, which means that average 6.06 kg of butylaldehydes was produced per 1 hour. The conversion efficiency was 95.6%, in which the conversion efficiency means the conversion rate from the injected propylene to butylaldehydes, not from the injected propylene to propane that is a by-product.

Comparative Example 2

The hydrogenation reaction was continuously performed with the same method to Example 1.3.2, except packing by using only the nickel catalyst that was put in the gamma-alumina as a catalyst. As a result, the driving was performed for 72 hours after reaching the normal state, and 465 kg of the total amount of the hydrogenation reaction product having butylalcohol as a main component was produced, which means that average 6.46 kg of butanol was produced per 1 hour.

From analyzing the components through the gas chromatography, normal-butylalcohol was 84.8%, iso-butylalcohol was 8.7%, and water was 0.2%, but a heavy component, such as butylaldehyde trimer, was 6.3% as a weight rate.

Comparative Example 3

Two packed columns having 20 plates of theoretical plate number were connected in series, in which the packed columns were installed with the reboiler and the condenser using the pipe with the same diameter and length to Example 1.3. While Feed as the same to Example 1.3 was also supplied in a flow rate of 6.4 kg per 1 hour to 8th plate from the upper part of the first column as the same method to Example 1.3, the product was recovered from a tower top and the product recovered from a tower bottom was again injected to 8th plate from the upper part of the second column; and also the products were recovered from the tower top and bottom of the second column.

The driving time of the normal state was for 70 hours, 0.89 kg of total water and less than 15 g of iso-butylalcohol were obtained as the product from the tower top of the first column. The tri-component mixture containing 38.7 kg of iso-butylalcohol, 388.3 kg of normal-butylalcohol, and 7 g of water was obtained as the product from the tower top of the second column. 18.6 kg of aldehyde trimer and 0.7 kg of normal-bytylalcohol were obtained as the final product from the tower bottom.

As a result of changing from the energy amount that was supplied from the reboiler to the column to the caloric value under the driving condition of the normal state, the total caloric value was 1.93 Mcal/hr, which means average 0.63 Mcal per 1 hour was in the first column and average 1.32 Mcal per 1 hour was in the second column.

The invention claimed is:

1. An apparatus for producing alcohols, comprising:
a hydroformylation reactor comprising: a nozzle for spraying olefins and a synthesis gas (CO/H2) toward a catalyst mixture solution inside the hydroformylation reactor;
a reactor outlet for discharging a reaction mixture of the olefins and the synthesis gas; and
a distributor plate for converting a flow of the olefins and the synthesis gas ($CO/H_2$), in which the distributor plate is installed between the nozzle for spraying the olefins and the synthesis gas ($CO/H_2$) toward a catalyst mixture solution inside the hydroformylation reactor and the reactor outlet, and
a hydrogenation reactor for producing alcohols by adding hydrogen to the recovered aldehydes from the hydroformylation reactor,
wherein the hydrogenation reactor comprises: a nozzle for spraying the recovered aldehydes and hydrogen gas from the hydroformylation reactor inside the hydrogenation reactor; a nickel catalyst layer having a high activity, in which the nickel catalyst layer is located at a site of flowing aldehydes and hydrogen; a copper catalyst layer having a low activity, in which the copper catalyst layer is located after the nickel catalyst layer; and a reactor outlet for discharging the hydrogenation reaction mixture, in which the reactor outlet is located after the copper catalyst layer.

2. The apparatus for producing alcohols of claim 1, wherein the hydroformylation reactor comprises circulation pipes for circulating the reaction mixture by recovering the reaction mixture from the reactor outlet and then resupplying to the nozzle for spraying the olefins and the synthesis gas ($CO/H_2$) toward the catalyst mixture solution inside the hydroformylation reactor, in which the hydroformylation reactor is connected to the reactor outlet and the nozzle for spraying the olefins and the synthesis gas ($CO/H_2$) toward the catalyst mixture solution inside the hydroformylation reactor.

3. The apparatus for producing alcohols of claim 2, wherein the hydroformylation reactor is connected to a catalyst/aldehydes separator comprising:
a separation pipe for separating the reaction mixture from the circulation flow in the circulation pipes, in which the separation pipe is connected to one of the circulation pipes;
a catalyst/aldehydes separation machine for separating the catalyst mixture solution and aldehydes from the reaction mixture, in which the catalyst/aldehydes separation machine is connected to the separation pipe;
a supplying pipe of the catalyst mixture solution for transferring the catalyst/aldehydes separation machine; and
an aldehyde recovering pipe for recovering aldehydes, in which the aldehyde recovering pipe is connected to the catalyst/aldehydes separation machine.

4. The apparatus for producing alcohols of claim 1, wherein the hydrogenation reactor is connected to a distillation column comprising:
an inlet part for entering the hydrogenation reaction product passed through the hydrogenation reactor;
a low boiling point component outlet part for discharging the low boiling point component among the hydrogenation reaction products;
a middle boiling point component outlet part for discharging the meddle boiling point component among the hydrogenation reaction products; and
a high boiling point component outlet part for discharging the high boiling point component among the hydrogenation reaction products.

5. The apparatus for producing alcohols of claim 1, wherein the hydrogenation reactor comprises a loop reactor or dual fixed reactors.

6. The apparatus for producing alcohols of claim 1, wherein the nozzle of the hydroformylation reactor comprises an ejector installed with the nozzle.

7. The apparatus for producing alcohols of claim 1, wherein the nozzle of the hydroformylation reactor comprises a venturi tube.

8. The apparatus for producing alcohols of claim 7, wherein the venturi tube comprises an inlet part for entering the olefins and the synthesis gas and a diffusion part, in which the diffusion part is connected to the inlet part; and
the diameter of the diffusion part inlet is the same to the diameter of the inlet part tube, and the diameter of the diffusion part outlet is 1.0 to 10 times longer than that of the diffusion part inlet.

9. The apparatus for producing alcohols of claim 1, wherein the distributor plate is located between ½ and ⅔ of the length from the end of the nozzle to the reactor outlet.

10. The apparatus for producing alcohols of claim 1, wherein the hydrogenation reactor comprises:
the nozzle for spraying the recovered aldehydes and hydrogen gas from the hydroformylation reactor inside the hydrogenation reactor to a catalyst mixture solution that is charged inside the reactor;
the reactor outlet for discharging the hydrogenation reaction mixture of aldehydes and hydrogen gas, in which the reactor outlet is located at the bottom of the reactor; and
a circulation pipe for circulating the reaction mixture by recovering the reaction mixture from the reactor outlet and then supplying them to the nozzle, in which the circulation pipe is connected to the reactor outlet and the nozzle.

11. The apparatus for producing alcohols of claim 10, wherein the nozzle of the hydrogenation reactor comprises the ejector installed with the nozzle.

12. The apparatus for producing alcohols of claim 10, wherein the nozzle of the hydrogenation reactor comprises the venturi tube.

13. The apparatus for producing alcohols of claim 12, wherein the venturi tube comprises an inlet part for entering the olefins and the synthesis gas and a diffusion part, in which the diffusion part is connected to the inlet part; and
the diameter of the diffusion part inlet is the same to the diameter of the inlet part tube, and the diameter of the diffusion part outlet is 1.0 to 10 times longer than that of the diffusion part inlet.

14. The apparatus for producing alcohols of claim 13, wherein the length of the venturi diffusion part is 0.01 to 0.95 times longer than that of the reactor.

* * * * *